United States Patent [19]

Conrad et al.

[11] 4,199,504

[45] Apr. 22, 1980

[54] BRIDGED CATHRANTHUS ALKALOID DIMERS

[75] Inventors: Robert A. Conrad; Koert Gerzon, both of Indianapolis, Ind.

[73] Assignee: Eli Lilly and Company, Indianapolis, Ind.

[21] Appl. No.: 905,667

[22] Filed: May 15, 1978

[51] Int. Cl.$^2$ ............................................ C07D 519/04
[52] U.S. Cl. ................................................. 260/244.4
[58] Field of Search ......................... 260/287 B, 244.4

Primary Examiner—Donald G. Daus
Assistant Examiner—David E. Wheeler
Attorney, Agent, or Firm—James L. Rowe; Arthur R. Whale

[57] ABSTRACT

Bridged vinca dimers in which two indole-dihydroindole C-3 carboxamides are linked through the nitrogen atom of a carboxamide group, useful as oncolytic agents.

6 Claims, No Drawings

BRIDGED CATHRANTHUS ALKALOID DIMERS

BACKGROUND OF THE INVENTION

Several naturally-occurring alkaloids obtainable from *Vinca rosea* (*Catharanthus roseus don.*-Catharanthus or Vinca alkaloids) have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leuroformine (Belgian Pat. No. 811,110); leurosidine (vinrosidine) and leurocristine (to be referred to hereafter as vincristine) (both in U.S. Pat. No. 3,205,220); deoxy VLB "A" and "B", *Tetrahedron Letters*, 783 (1958); 4-desacetoxyvinblastine (U.S. Pat. No. 3,954,773; 4-desacetoxy-3'-hydroxyvinblastine (U.S. Pat. No. 3,944,554); leurocolombine (U.S. Pat. No. 3,890,325) and vincadioline (U.S. Pat. No. 3,887,565). Two of these alkaloids, VLB and vincristine, are now marketed as drugs for the treatment of malignancies, particularly the leukemias and related diseases in humans. The two marketed alkaloids are customarily administered by the i.v. route.

Chemical modification of the Vinca alkaloids has been rather limited. In the first place, the molecular structures involved are extremely complex, and chemical reactions which modify one specific functional group of the molecule without affecting other groups are difficult to develop. Secondly, dimeric alkaloids lacking desirable chemotherapeutic properties have been recovered or produced from *Vinca rosea* fractions or alkaloids, and a determination of their structures has led to the conclusion that these compounds are closely related to the active alkaloids, frequently differing only as to stereochemistry at a single carbon. Thus, anti-neoplastic activity seems to be limited to very specific basic structures, and the chances of obtaining more active drugs by modification of these structures would seem to be correspondingly slight. Among the successful modifications of physiologically-active alkaloids has been the preparation of 6,7-dihydro VLB (U.S. Pat. No. 3,352,868) and the replacement of the acetyl group at C-4 (carbon no. 4 of the VLB ring system-see the numbered structure below) with higher alkanoyl group or with unrelated acyl groups. (See U.S. Pat. No. 3,392,173.) Several of these C-4 derivatives are capable of prolonging the life of mice inoculated with P1534 leukemia. One of the C-4 derivatives in which a chloracetyl group replaces the C-4 acetyl group of VLB is also a useful intermediate for the preparation of structurally modified VLB compounds in which an N,N-dialkylglycyl group replaces the C-4 acetyl group of VLB (See U.S. Pat. No. 3,387,001). C-3 carboxamide and carboxhydrazide derivatives of VLB, vincristine, vincadioline etc. have also been prepared and found to be active anti-tumor agents (see Belgian No. 813,168). These compounds are extremely interesting because, for example, the 3-carboxamides of VLB are more active against Ridgeway osteogenic sarcoma and Gardner lymphosarcoma than is VLB, the basic alkaloid from which they are derived. Certain of these amide derivatives actually approach the activity of vincristine against these tumors. In particular, 4-desacetyl VLB C-3 carboxamide (vindesine) is currently on clinical trial in humans, where it appears to have less neurotoxicity than does vincristine and to be effective against leukemias including vincristine-resistant leukemias.

The copending application of Cullinan and Gerzon, Ser. No. 828,693 filed Aug. 29, 1977, discloses and claims bridged bis vinca dimers which can be represented by the formula R—NH—CH$_2$—(CH$_2$)$_n$—S—S—CH$_2$—(CH$_2$)$_n$—NH—R wherein R is a residue of a dimeric C-3 carbonyl-containing vinca alkaloid with oncolytic activity and n is 1–5. Compounds of this structure were found to be the chief product of the reaction of a vinca C-3 carboxazide (R—N$_3$) and NH$_2$—CH$_2$—CH$_2$—SH and are believed to arise by air oxidation of the C-3 carboxamidoethyl mercaptan group, as in the cysteine—cystine system. This oxidation is, of course, limited to the formation of a disulfide link from a mercaptoalkylamide, and is not generally applicable to the synthesis of other bridged bis Catharanthus dimers.

SUMMARY OF THE INVENTION

This invention provides vinca tetramers (dimers of indole-dihydroindoles) of the formula:

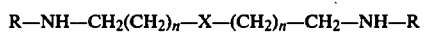

R—NH—CH$_2$(CH$_2$)$_n$—X—(CH$_2$)$_n$—CH$_2$—NH—R wherein each R is the same or different residue of an indoledihydroindole alkaloid of the formula:

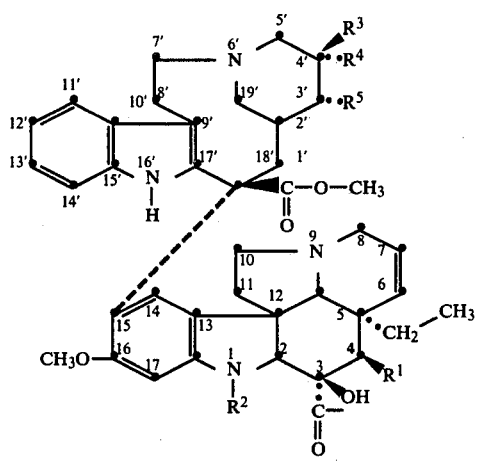

wherein
R$^1$ is OH or O—CO—CH$_3$;
R$^2$ is CH$_3$, H or CHO:
one of R$^3$ and R$^4$, when taken singly, is H or OH and the other is C$_2$H$_5$ and R$^5$ is H; and
when taken together, R$^4$ and R$^5$ form an α-epoxide ring and R$^3$ is C$_2$H$_5$;
X is S, Se—Se, O, NH, N—[(CH$_2$)$_m$—CH$_2$—NH—R] or (CH$_2$)$_p$ wherein m is 1 or 2 and each n and p are individually 0, 1, 2, 3 or 4; and
pharmaceutically-acceptable acid addition salts thereof.

In the product: R—NH—CH$_2$—(CH$_2$)$_n$—X—(CH$_2$)$_n$—CH$_2$—NH—R, in R (formula I above) where R$^1$ is acetoxy, R$^2$ is methyl, R$^3$ is hydroxy, R$^4$ is ethyl and R$^5$ is H, a VLB amide is represented; where R$^1$ is acetoxy, R$^2$ is formyl, R$^3$ is hydroxyl, R$^4$ is ethyl and R$^5$ is H, a vincristine amide is represented; where R$^1$ is acetoxy, R$^2$ is methyl, R$^3$ is ethyl, R$^4$ is hydroxyl and R$^5$ is H, a leurosidine amide is represented; where R$^1$ is acetoxy, R$^2$ is methyl, R$^3$ and R$^5$ are H and R$^4$ is ethyl, a deoxy VLB "A" amide is represented; where R$^1$, R$^2$ and R$^5$ are the same as in deoxy VLB "A" but R$^3$ is ethyl and R$^4$ is hydrogen, a deoxy VLB "B" amide is represented;

where $R^1$ is acetoxy, $R^2$ is methyl, $R^3$ is ethyl and $R^4$ and $R^5$ taken together form an α-epoxide ring, a leurosine amide is represented; and where both R groups are identical, a bis amide is represented.

Compounds of this invention, in which, in the residue of the indole-dihydroindole alkaloid (R), $R^2$ is H are intermediates which are formylated to yield an oncolytic agent in which $R^2$ is CHO.

Non-toxic acids useful for forming pharmaceutically-acceptable acid addition salts of the compounds of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts of non-toxic organic acids including aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include the sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acylate, formate, isobutyrate, caprate, heptanoate, propiolate, oxalate, malonate, succinate, suberate, sebacate, fumarate, maleate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

Illustrative compounds coming within the scope of this invention include:

bis[β-(VLB C-3 carboxamido)ethyl]sulfide disulfate
bis[γ-(4-desacetyl-4'-deoxy VLB C-3 carboxamido)propyl]ether
1,5-bis(4-desacetylleurosidine C-3 carboxamido)pentane
1,2-bis(leurosine C-3 carboxamido)ethane
bis[γ-(4'-deoxyleurosidine C-3 carboxamido)propyl]diselenide
bis[β-(4'-deoxyvincristine C-3 carboxamido)ethyl]sulfide disulfate
bis[β-(4-desacetyl-4'-deoxy-1-desmethyl-1-formyl-leurosidine C-3 carboxamido)ethyl]ether disulfate
tris [β-(VLB C-3 carboxamido)ethyl]amine
$N^1$-(4-desacetyl-VLB-3-carbonyl)-$N^2$-(VLB 3-carbonyl)octamethylenediamine
1,8-bis(4'-deoxy VLB C-3 carboxamido)octane
1,11-bis(4-desacetylvincristine C-3 carboxamido)undecane
1,14-bis(4-desacetylleurosine C-3 carboxamido)tetradecane
$N^1$-(4'-deoxyleurosidine 3-carbonyl)-$N^2$-(4'-deoxy VLB 3-carbonyl)-bis(β-aminoethyl)sulfide
$N^1$-(4-desacetylvincristine 3-carbonyl)-$N^2$-(4-desacetyl VLB 3-carbonyl)-bis(β-aminoethyl)ether
$N^1$-(4-desacetyl VLB 3-carbonyl)-$N^2$-(4-desacetylleurosidine 3-carbonyl)-bis(4-aminobutyl)diselenide.

This invention also provides a method of preparing the above compounds as well as an improved method of preparing certain vinca tetramers disclosed and claimed in the copending application of Cullinan and Gerzon, Ser. No. 828,693 filed Aug. 29, 1977. This process is a method of synthesizing a compound of the formula $R^6$—NH—CH$_2$—(CH$_2$)$_n$—Q—(CH$_2$)$_n$—CH$_2$—NH—$R^6$ wherein each $R^6$ is the residue of an indole-dihydroindole alkaloid of the formula:

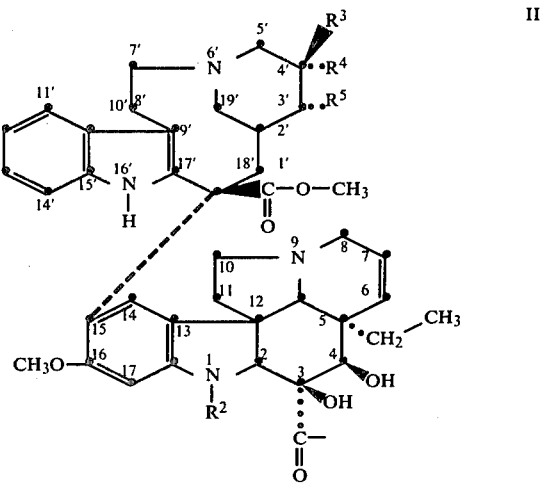

wherein
$R^2$ is CH$_3$ or H;
when taken singly, one of $R^3$ and $R^4$ is OH or H and the other is C$_2$H$_5$ and $R^5$ is H; and when taken together $R^4$ and $R^5$ form an α-epoxide ring and $R^3$ is C$_2$H$_5$; and
Q is S, S—S, O, Se—Se, NH, N—[(CH$_2$)$_m$—CH$_2$—NH—$R^6$] or (CH$_2$)$_p$ wherein each n and p are 0, 1, 2, 3 or 4 and m is 1 or 2, which comprises reacting an azide of the formula $R^6$—N$_3$ with a diamine or triamine of the formula NH$_2$—CH$_2$—(CH$_2$)$_n$—Q—(CH$_2$)$_n$—CH$_2$—NH$_2$ wherein Q is S, S—S, O, Se—Se, NH, N—(CH$_2$)$_m$—CH$_2$—NH$_2$ or (CH$_2$)$_p$ wherein m is 1 or 2 and each n or p are 0, 1, 2, 3 or 4, in the ratio of two moles of $R^6$—N$_3$ per mole of diamine when Q is S, S—S, Se—Se, O, NH or (CH$_2$)$_p$ and three moles of $R^6$—N$_3$ per mole of triamine where Q is N—(CH$_2$)$_m$—CH$_2$—NH$_2$.

The first step in the preparation of the compounds of Formula II, is carried out by mixing the azide, $R^6$—N$_3$, in a suitable inert solvent, customarily methylenedichloride, with the diamine or triamine NH$_2$—CH$_2$—(CH$_2$)$_n$—Q—(CH$_2$)$_n$—CH$_2$—NH$_2$ wherein Q has the same meaning as hereinabove, in the ratio of 2 moles of azide per mole of diamine or 3 moles of azide per mole of triamine. The diamine or triamine is also dissolved in an inert solvent, usually methylene dichloride, prior to addition. As pointed out below, since the azide ordinarily is not purified but used as isolated from the reaction mixture, that solvent in which it is isolated is conveniently employed for the reaction with the diamine or triamine. The bis or tris vinca amide thus produced is isolated by standard techniques and purified by chromatography.

The compounds of this invention according to the Formula I above are prepared by the following synthetic procedure in which the above novel process is the final step. Using VLB as exemplary of the synthetic procedure, VLB is reacted with anhydrous hydrazine in a mutual inert solvent such as a lower alkanol in a sealed reaction vessel. The reaction mixture is customarily heated in the range 40°–100° C. for periods of from 12 to 48 hours during which time the reaction is substantially complete. The product of the reaction is 4-desacetyl VLB C-3 carboxhydrazide since the reaction of hydrazine not only serves to convert the ester group at C-3 to a hydrazide group, but also, under the basic reaction condition, serves to hydrolyze the acetyl at C-4 to yield a hydroxyl. Other ester groups in the molecule are not affected by the above reaction conditions, except that a quantity of the 18'-descarbomethoxy derivative is ordinarily produced. However, the main product of the reaction is 4-desacetyl VLB C-3 carboxhydrazide. The 4-desacetyl C-3 carboxhydrazide derivatives of deoxy VLB "A" and "B", of leurosidine and of leurosine are produced similarly. The carboxhydrazides thus produced are next converted to the corresponding azides by treatment with sodium nitrite in acid. The product of this reaction is ordinarily used as isolated from the reaction since it has been found that it is not necessary to purify the azide in order to obtain proper yields of the desired bisamide.

Reaction of two moles of the 4-desacetyl C-3 carboxazides of VLB, leurosidine, deoxy VLB "A" and "B", leurosine and other alkaloids of the structure $R^6$-$OCH_3$ wherein $R^6$ is represented by Formula II (except that $R^2$ is $CH_3$ or H only), with the diamine $NH_2$—$CH_2$—$(CH_2)_n$—Q—$(CH_2)_n$—$CH_2$—$NH_2$ wherein Q is defined as above except for the grouping $N[(CH_2)_m$—$CH_2$—$NH_2]$ under the standard azide-amine reaction conditions of Belgian Pat. No. 813,168 for the preparation of monoamides of the same vinca alkaloids, yields the desired products $R^6$—NH—$CH_2$—$(CH_2)_n$—Q—$(CH_2)_n$—$CH_2$—NH—$R^6$ which includes those products of this invention according to the formula R—NH—$CH_2$—$(CH_2)_n$—X—$CH_2(CH_2)_n$—NH—R, R being defined by Formula I wherein $R^1$ is OH, $R^2$ is $CH_3$ and X is as defined except for the grouping N—$[(CH_2)_m$—$CH_2$—NH—R], and those products wherein $R^2$ is H other groups being the same, which must be formylated ($R^2$ is CHO) to yield an oncolytic agent of this invention.

When a tetramine reactant $NH_2$—$CH_2$—$(CH_2)_n$—Q—$(CH_2)_n$—$CH_2$—$NH_2$ wherein Q is N—$[(CH_2)_m$—$CH_2$—$NH_2]$ is employed, three moles of azide are employed per mole of tetramine and the final product is a tris-amide of the structure $[R^6$—NH—$CH_2$—$(CH_2)_n]_2$ N—$(CH_2)_m$—$CH_2$—NH—$R^6$.

Reaction of vincristine, leuroformine or other alkaloids represented by $R^6$—$OCH_3$ wherein $R^2$ is CHO, with hydrazine results not only in hydrolysis of the C-4 acetoxy to give a C-4 hydroxyl but also in deformylation at N-1. The product of this reaction, 1-desformyl-4-desacetyl vincristine C-3 carboxhydrazide for example, can be transformed to the azide and two or three moles of the azide reacted with one mole of $NH_2$—$CH_2$—$(CH_2)_n$—Q—$(CH_2)_n$—$CH_2$—$NH_2$ wherein Q and n have their previous meaning to yield a compound of the formula $R^6$—NH—$CH_2$—$(CH_2)_n$—Q—$(CH_2)_n$—$CH_2$—NH—$R^6$, in which $R^6$ has its previous meaning except that $R^2$ is H only. This compound must then be reformylated by standard procedures to yield the compound of this invention, $R^6$—NH—$CH_2$—$(CH_2)_n$—Q—$(CH_2)_n$—$CH_2$—NH—$R^6$, wherein $R^2$ is CHO.

Alternatively, those compounds of this invention in which $R^2$ (in $R^6$) is CHO can be prepared by low temperature (−60° C.) oxidation of the corresponding compound in which $R^2$ is $CH_3$ with $CrO_3$ in acetic acid and acetone. Bis amides containing an oxidizable group (—S—, —S—S—, —Se—Se— etc.) are not suitable substrates for this procedure and should be prepared by the method of the above paragraph.

Compounds according to Formula I above in which R represents two different moieties are prepared as follows: one mole of azide $R^6$—$N_3$ is reacted with one mole of diamine $NH_2$—$CH_2$—$(CH_2)_n$—Q—$(CH_2)_n$—$CH_2$—$NH_2$ to yield a half amide, $R^6$—NH—$CH_2$—$(CH_2)_n$—Q—$(CH_2)_n$—$CH_2$—$NH_2$.

These half-amides are readily separable from any bis-amide concomitantly prepared and can be purified and characterized by conventional means. In fact, a half-amide fraction is customarily obtained in addition to the bisamide as a by-product even when two moles of an azide are reacted with one mole of diamine. One mole of the half-amide is then reacted with one mole of a second azide $R^6$—$N_3$, in which the $R^6$ group is different from the one already present in the half-amide, $R^6$—NH—$CH_2$—$(CH_2)_n$—Q—$(CH_2)_n$—$CH_2$—$NH_2$ to yield an unsymmetrically substituted the bis amide. The unsymmetrical amides containing two different R groups which are not directly synthesizeable by the above procedures can be prepared by acetylating at C-4 or formylating at N-1, using conventional procedures, an unsymmetrical bis amide prepared as above lacking one or both of those features. The chief utility of these half-amides is as intermediates.

Starting materials useful in this synthetic procedure are prepared according to the following procedures.

PREPARATION OF STARTING MATERIALS

4-Desacetyl VLB C-3 Carboxhydrazide

VLB was heated in anhydrous ethanol with an excess of anhydrous hydrazine in a sealed reaction vessel at about 60° C. for about 18 hours. The reaction vessel was cooled, and opened, the contents removed, and the volatile constituents evaporated therefrom in vacuo. The resulting residue, comprising 4-desacetyl VLB C-3 carboxhydrazide, was taken up in methylene dichloride, the methylene dichloride solution washed with water, separated and dried, and the methylene dichloride removed by evaporation in vacuo. The resulting residue was dissolved in a 1:1 chloroform:benzene solvent mixture and chromatographed over silica gel. A benzene-chloroform-triethylamine eluant was employed to develop the chromatogram. The initial chromatographic fractions contained unreacted starting materials plus 4-desacetyl VLB produced as a by-product of the reaction. Further fractions were found to contain 4-desacetyl 18'-descarbomethoxy VLB C-3 carboxhydrazide previously described by Neuss et al., *Tetrahedron Letters*, 1968, 783. The succeeding fractions, found to contain 4-desacetyl VLB C-3 carboxhydrazide by thin layer chromatography, were combined, and the solvents evaporated therefrom in vacuo. The resulting solid melted at about 219°–220° C. with decomposition.

Following the above procedure, 4-desacetyl VLB also can be reacted with hydrazine to form 4-desacetyl VLB C-3 carboxhydrazide and leurocristine or 4-desacetyl leurocristine (available from Hargrove U.S. Pat. No. 3,392,173) can be reacted with anhydrous hydrazine in anhydrous ethanol to yield 4-desacetyl 1-desformyl leurocristine C-3 carboxhydrazide, isolated as an amorphous powder. 4-Desacetyl C-3 carboxhydrazides of the deoxy VLB's, of leurosidine and of leurosine are prepared in analogous fashion.

4-Desacetyl VLB C-3 Carboxazide

A solution of 678 mg. of 4-desacetyl VLB C-3 carboxhydrazide was prepared in 15 ml. of anhydrous methanol. About 50 ml. of 1 N aqueous hydrochloric acid were added, and the resulting solution cooled to about 0° C. Approximately 140 mg. of sodium nitrite were then added, and the resulting reaction mixture stirred for 10 minutes while maintaining the temperature at about 0° C. The solution turned dark red-brown upon the addition of the sodium nitrite. The reaction mixture was next made basic by the addition of an excess of cold 5 percent aqueous sodium bicarbonate. The aqueous solution was extracted three times with methylene dichloride. 4-Desacetyl VLB C-3 carboxazide formed in the above reaction passed into the methylene dichloride which layer was separated. The methylene dichloride solution of 4-desacetyl vinblastine C-3 carboxazide thus obtained is ordinarily used without further purification.

4-Desacetyl C-3 carboxazides of 1-desformylvincristine, leurosidine, 4'-deoxy VLB "A" and "B" and leurosine are prepared in analogous fashion.

This invention is further illustrated by the following specific examples:

EXAMPLE 1

Preparation of Bis[$\beta$-(4-desacetyl VLB C-3 carboxamidoethyl]disulfide

Eight grams of 4-desacetyl VLB C-3 carboxhydrazide in aqueous hydrochloric acid were reacted with sodium nitrite to form 4-desacetyl VLB C-3 carboxazide. The azide product of the reaction was isolated as a solution in 400 ml. of methylene dichloride.

Cystamine dihydrochloride (22.5 g.) was added to 500 ml. of methanol, containing dissolved therein 10.8 g. of sodium methoxide. The reaction mixture was stirred for about 4 hours after which time the solvent was removed by evaporation. The residue was stirred with ether for about 1 hour and then filtered. The ethereal filtrate was evaporated to dryness in vacuo leaving yielding about 10 g. of cystamine free base as an oily residue.

Cystamine free base (760 mg.) in methylene dichloride was added to the solution of the 4-desacetyl VLB C-3 carboxazide in methylene dichloride. 75 ml. of tetrahydrofuran were added, and the reaction stirred in the dark for about 16 hours at ambient temperature. The reaction mixture was then filtered and the filtrate evaporated to dryness in vacuo. The resulting residue containing bis[$\beta$-(4-desacetyl VLB C-3 carboxamido)ethyl]disulfide was dissolved in methylene dichloride. The methylene dichloride solution was washed with water and then dried. Evaporation of the methylene dichloride yielded a residue which was shown to contain 2 major products by TLC (1:1:1 methylene dichloride-methanol-ethyl acetate). The residue was then chromatographed over silica using the same solvent system as the eluant. Fractions shown by TLC to contain bis[$\beta$-(4-desacetyl VLB C-3 carboxamido)ethyl]disulfide were combined and the solvents evaporated therefrom. The other major product of the reaction was also separated and purified and proved to be the reaction product of 1 mole of 4-desacetyl VLB C-3 carboxazide and cystamine, 4-desacetyl VLB C-3 N-2-(2-aminoethyldithio)ethyl carboxamide. Higher yields of this 1:1 product are obtained if one mole of azide is reacted with one mole of cystamine. Bis[$\beta$-(4-desacetyl VLB C-3 carboxamido)ethyl]disulfide thus prepared was identical to that obtained by the procedure described in Ser. No. 828,693, filed Aug. 29, 1977.

The disulfate salt of bis[$\beta$-(4-desacetyl VLB C-3 carboxamido)ethyl]disulfide was prepared in ethanol by the stoichiometric addition of 2 percent (V/V) ethanolic sulfuric acid. The disulfate was also prepared by titrating a solution of the base with 2 percent ethanolic sulfuric acid to the point where an aliquot of the solution diluted with 5 volumes of water had a pH in the range 3.0°–3.5° C. Either method of preparation yielded an off-white amorphous salt after evaporation of the ethanol.

Following the above procedure, 4-desacetyl VLB C-3 carboxazide was reacted with hexamethylenediamine in a 2:1 molar ratio to yield 1,6-bis(4-desacetyl VLB C-3 carboxamido)hexane having the following physical characteristics:

Molecular spectrum; m/e 768 (cleavage of hexamethylene $\alpha,\beta$ bond to give essentially an N-methyl vindesine species)

Infrared spectrum; $\nu$ (CHCl$_3$) 1730 and 1660 cm$^{-1}$.

Titration (66 percent DMF); pK$_a$' 5.27, 7.27.

Osmotic molecular weight in 1,2-dichlorethane = 1422 (calculated 1588).

$^{13}$CNMR; 173.4 ppm. (indicative of secondary amide); all other peaks similar to those found for vindesine with additional of peaks at 26.6, 29.3, and 39.0 ppm. (hexamethylene bridge).

Following the above procedure, 4-desacetyl VLB C-3 carboxazide was reacted with bis(2-aminoethyl)sulfide in a 2:1 molar ratio to yield bis[$\beta$-(4-desacetyl VLB C-3 carboxamido)ethyl]sulfide having the following physical characteristics:

Osmotic molecular weight = 1646 (calculated 1592);

Infrared spectrum $\nu$ (CHCl$_3$) 1730 and 1660 cm$^{-1}$.

Mass spectrum; m/e 827 (—S—methyl species).

Elemental analysis: sulfur calculated 2.00, found 1.75.

$^{13}$CNMR; same as for vindesine except peaks at 173.7 ppm. (secondary amide) and extra peaks at 38.6 and 32.9 ppm.

Following the above procedure, 4-desacetyl VLB C-3 carboxazide was reacted in a 2:1 molar ratio with butylenediamine to yield 1,4-bis(4-desacetyl VLB C-3 carboxamido)butane having the following physical characteristics: mass spectrum; m/e 808 (butyl amide) 767 (methyl amide);

Titration; (66% DMF) pK$_a$' 6.6, 7.5;

Infrared spectrum; $\nu$ (CHCl$_3$) 1730, 1665 cm$^{-1}$

Osmotic molecular weight = 1195 (calculated 1582).

Following the above procedure, 4-desacetyl VLB C-3 carboxazide was reacted with bis($\beta$-aminoethyl)-diselenide in a 2:1 molar ratio to yield bis[$\beta$-(4-desacetyl VLB C-3 carboxamido)ethyl]diselenide having the following physical characteristics:

$^{13}$CNMR; same as vindesine but with secondary amide peak at 173.6 and extra peaks at 39.6 and possibly 38.2 ppm.

Titration (66% DMF); pK$_a$' 5.10, 7.22;

Infrared spectrum; $\nu$ (CHCl$_3$) 1735 and 1670 cm$^{-1}$;

Mass spectrum; peaks at 873–875 and 815–817 (isotopes of $^{78}$Se and $^{80}$Se).

Following the above procedure, 4-desacetyl VLB C-3 carboxazide was reacted with bis($\beta$-aminoethyl)ether in a 2:1 molar ratio to yield bis[$\beta$-(4-desacetyl VLB C-3 carboxamido)ethyl]ether having the following physical characteristics:

Infrared spectrum; ν (CHCl₃) 1730 and 1665 cm⁻¹.
Titration (66 percent DMF); p$K_a'$ 5.13, 7.21;
Mass spectrum; m/e 796.

Following the above procedure, 4-desacetyl VLB C-3 carboxazide was reacted with bis(γ-amino)propyl disulfide to yield bis[γ-(4-desacetyl VLB C-3 carboxamido)propyl]disulfide having the following physical characteristics:

Elemental analysis; sulfur calculated 3.72; found 3.87;
Molecular spectrum; m/e 841, 855;
Titration (66% DMF); p$K_a'$ 5.20, 7.21;
Infrared spectrum; ν (CHCl₃) 1730 and 1670 cm⁻¹.
¹³CNMR; same as for vindesine except secondary amide at 173.7 and extra peaks at 42.0, 36.0, and 39.2.

Following the above procedure, 4-desacetyl VLB C-3 carboxazide was reacted with bis(γ-aminopropyl)amine in a 2:1 molecular ratio to yield bis[γ-(4-desacetyl VLB C-3 carboxamido)propyl]amine having the following physical characteristics:

Osmotic molecular weight=1999 (calculated 1603);
Titration (66% DMF); p$K_a'$ 4.98, 7.17, 10.18;
Infrared spectrum; ν (CHCl₃) 1730 and 1660 cm⁻¹.
¹³CNMR; same as for vindesine with an amide resonance at 174.2 and extra resonances at 39.3 and 37.0 ppm.

Following the above procedure, 4-desacetyl leurosine C-3 carboxazide was reacted with cystamine in a 2:1 molar ratio to yield bis[β-(4-desacetyl leurosine C-3 carboxamido)ethyl]disulfide having the following physical characteristics:

Mass spectrum; m/e 825;
Infrared spectrum; ν (CHCl₃) 1730 and 1670 cm⁻¹.
Titration (66% DMF); p$K_a'$ 5.3 and 7.0.
Osmotic molecular weight; 1479 (calculated 1620),
¹³CNMR; similar to vindesine with amide at 173.7 (secondary) an extra resonances at 39.2 and 37.5 ppm.

Following the above procedure, 4-desacetyl VLB C-3 carboxazide was reacted with tris (β-aminoethyl)amine in a 3:1 molar ratio to yield tris [β-(4-desacetyl VLB C-3 carboxamido)ethyl]amine having the following physical characteristics:

Osmotic molecular=weight 2262 (calculated 2354)
Infrared spectrum; ν (CHCl₃) 1730 and 1660 cm⁻¹.
Titration (66% DMF); p$K_a'$ 5.2 and 7.25.

Other vinca tetramers in which two dimeric indoledihydroindole alkaloids are linked through the C-3 carboxyl group to form a bis amide, with the two amide groups being linked by alkyl chains which can be interrupted by sulfur, selenium, oxygen or nitrogen, are prepared in similar fashion.

EXAMPLE 2

Preparation of 1,4-Bis(4-desacetyl vincristine C-3 carboxamido)butane 1 g. of 1,4-Bis(4-desacetyl VLB C-3 carboxamido)butane was dissolved in 10 ml. of methylene dichloride and 120 ml. of acetone. The solution was cooled to −61° C. whereupon 4 ml. of acetic acid were added followed by the dropwise addition of a solution of 2 g. of chromic oxide, 2 ml. of water and 10 ml. of acetic acid. The reaction mixture was stirred at about −60° C. for 1.5 hours and was then quenched by the addition of 14 N aqueous ammonium hydroxide. The resulting mixture was extracted with methylene dichloride, the methylene dichloride extract was separated and dried and the solvents evaporated therefrom in vacuo. The resulting residue, comprising 1,4-bis(4-desacetylvincristine C-3 carboxamido)butane, was purified by chromatography over silica using a 1:1:1 methylene dichlorideethyl acetate-methanol solvent mixture as the eluant. Fractions shown to contain 1,4-[bis(4-desacetylvincristine C-3 carboxamido)ethyl]butane thus prepared had the following physical characteristics:

Molecular spectrum; m/e 781 and 722, 371 and 355, 167, 154.
Infrared spectrum; ν (chloroform) 1740 and 1685 cm⁻¹.

Other compounds of this invention in which $R_2$ is formyl can be prepared from the corresponding compound in which $R_2$ is methyl by low temperature chromic acid oxidation. Alternatively, the procedure of reaction 1 can be followed except that 1-desformyl-4-desacetyl vincristine C-3 carboxazide is used as the starting material in place of the corresponding VLB compound and a reformylation step is necessary.

Compounds of this invention according to Formula I above in which $R^1$ is O—CO—CH₃ are prepared by acetylation of the corresponding derivative in which $R^1$ is OH by the procedure of Hargrove, *Lloydia*, 27, 340 (1964) or by careful acetylation with 2 moles of acetic anhydride per mole of tetramer followed by chromatography to separate any C-3 hydroxyl acetylation.

EXAMPLE 3

Preparation of Salts

Sulfate salts of the above amides are prepared by dissolving the particular amide in absolute ethanol and adjusting the pH of the resulting solution to about 3.0–3.5 with 2 percent ethanolic sulfuric acid. Other salts, including salts with inorganic ions such as chloride, bromide, phosphate, nitrate and the like as well as salts with organic ions such as benzoate, methanesulfonate, maleate, tartrate and the like are prepared in analogous fashion.

The compounds of this invention and those preparable by the process disclosed herein are active against transplanted tumors in mice in vivo. In demonstrating such activity of the drugs of this invention, a protocol was used which involved the administration of the drug, usually by the intraperitoneal route, at selected dose levels every day for 9–10 days, or every fourth day, after innoculation with the tumor.

The following table—Table 1—gives the results of experiments in which mice bearing transplanted Gardner lymphosarcoma (GLS), C₃H mammary tumor, B16 melanoma, P 1534(J) leukemia, P388 leukemia or 755 adenocarcinoma were treated with a compound of this invention. In the table, column 1 gives the name of the compound; column 2, the tumor system employed; column 3, the dosage schedule and column 4, the percent inhibition of tumor growth or increased life span.

In utilizing the novel compound of this invention as anti-tumor agents in mammals, the parenteral route of administration is conveniently employed. With parenteral administration, the intravenous route is preferred although with smaller mammals such as mice the intraperitoneal route may be used. For intravenous administration, isotonic solutions are employed containing 1–10 mg./ml. of a salt of an alkaloidal base of formula I above. The compounds are administered at a rate of from 0.01 to 1 mg./kg. and preferably from 0.1 to 1 mg./kg. of mammalian body weight once or twice a week or every two weeks depending on both the activity and the toxicity of the drug. An alternative method of arriving at a therapeutic dose is based on body-surface area with a dose in the range 0.1 to 10 mg./meter squared of mammalian body surface every 7 or 17 days.

Table 1

| Name of Compound | Tumor | mg./kg. × No. of Days | Percent Inhibition or Prolongation of Survival Time |
|---|---|---|---|
| 1,6-bis(4-Desacetyl VLB C-3 carboxamido)hexane disulfate | P388 | 1.2 × 3 | 74 |
| | | 0.9 × 3 | 27 |
| bis[β-(4-Desacetyl VLB C-3 carboxamido)ethyl]sulfide disulfate | P388 | 1.2 × 3 | 33 |
| | | 0.9 × 3 | 49 |
| | | 0.6 × 3 | 34 |
| bis[β-(4-Desacetyl VLB C-3 carboxamido)ethyl]diselenide disulfate | 755 | 1.8 × 3 | 89 |
| | | 1.2 × 3 | 31–42 |
| | | 0.9 × 3 | 21–62 |
| | | 0.6 × 3 | 26–32 |
| | P1534(J) | 1.8 × 3 | 66 |
| | | 1.2 × 3 | 21 |
| | $C_3H$ | 2.5 × 3 | Toxic |
| | | 2.0 × 3 | 72 |
| | | 1.5 × 3 | 56 |
| | GLS | 2.5 × 3 | 72 |
| | | 2.0 × 3 | 57 |
| | | 1.5 × 3 | 29 |
| bis[β-(4-Desacetylleurosine C-3 carboxamido)ethyl]disulfide disulfate | P388 | 30 × 3 | 55 |
| | | 15 × 3 | 46 |
| 1,4-bis(4-Desacetyl VLB C-3 carboxamido)butane disulfate | GLS | 0.4 × 9 | 40 |
| bis[β-(4-Desacetyl VLB C-3 carboxamido)ethyl]ether disulfate | P388 | 1.8 × 3 | Toxic |
| | | 1.2 × 3 | 85 |
| | | 0.9 × 3 | 77 |
| | | 0.6 × 3 | 53 |
| | GLS | 0.4 × 9 | 62 |
| bis[β-(4-Desacetyl VLB C-3 carboxamido)ethyl]disulfide disulfate | GLS | 0.4 × 9 | 43–100 |
| | | 1.2 × 3 | 62–93 |
| | | 0.9 × 3 | 34–46 |
| | $C_3H$ | 1.2 × 3 | Toxic |
| | | 0.9 × 3 | 31–36 |
| bis[β-desacetyl VLB C-3 carboxamido)ethyl]disulfide disulfate | P388 | 1.2 × 3 | 53–61 |
| | | 0.9 × 3 | 39–47 |
| | | 0.6 × 3 | 33–44 |
| | 755 | 1.6 × 3 | 60 |
| | | 1.2 × 3 | 67–8 |
| | | 0.9 × 3 | 34–54 |
| | | 0.6 × 3 | 29–34 |
| | P1534(J) | 1.6 × 3 | 90–99 |
| | | 1.2 × 3 | 62 or Toxic |
| | | 0.9 × 3 | 50–53 |
| | | 0.6 × 3 | 20–39 |
| | B16 | 0.6 × 3 | 118 (7)* |
| | | 0.9 × 3 | 86 (7) |
| | | 1.2 × 3 | 24 (3) |
| bis [γ-(4-desacetyl VLB C-3 carboxamido)propyl]disulfide disulfate | B16 | 0.6 × 3 | 99 (8) |
| | | 0.9 × 3 | 61 (5) |
| | | 1.2 × 3 | 68 (8) |

*number of indefinite survivors in parentheses.

In utilizing a compound of this invention clinically, the clinical physician would administer the compound initially by the same route and in the same vehicle and probably against the same types of tumors as are indicated for vincristine or VLB. The dose levels employed would reflect the difference in dose levels found in the treatment of experimental tumors in mice, the dose levels of the compounds of this invention being in general comparable to those used with vincristine and VLB in tumors sensitive to one or both of these drugs. In clinical tests, as with other anti-tumor agents, particular attention would be paid to the effect of the oncolytic compounds of this invention against the ten "signal" tumors set forth at page 266 of "The Design of Clinical Trials in Cancer Therapy" edited by Staquet (Futura Publishing Company, 1973).

We claim:

1. A compound of the formula

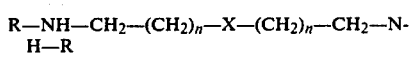

wherein each R is

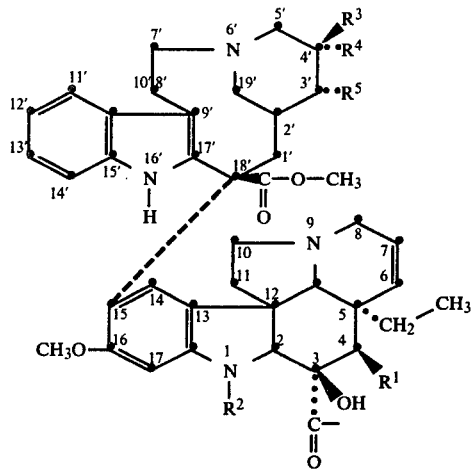

wherein $R^1$ is OH or O—CO—CH$_3$;
$R^2$ is CH$_3$, H or CHO;

when taken singly, one of $R^3$ and $R^4$ is H or OH, the other being C$_2$H$_5$, and $R^5$ is H; and when $R^4$ and $R^5$ are taken together, they form an α-epoxide ring and $R^3$ is C$_2$H$_5$;

X is S, O, Se—Se, or a bond wherein each n is 0, 1, or 2; and pharmaceutically-acceptable acid addition salts thereof.

2. A compound according to claim 1, said compound being bis[β-(4-desacetyl VLB C-3 carboxamido)ethyl]-diselenide.

3. A compound according to claim 1, said compound being bis[β-(4-desacetyl VLB C-3 carboxamido)ethyl]ether.

4. A compound according to claim 1, said compound being 1,6-bis(4-desacetyl VLB C-3 carboxamido)hexane.

5. A compound according to claim 1, said compound being 1,4-bis(4-desacetyl VLB C-3 carboxamido)butane.

6. A compound according to claim 1, said compound being bis[β-(4-desacetyl VLB C-3 carboxamido)ethyl]sulfide.

* * * * *